United States Patent [19]

Gemma et al.

[11] Patent Number: 5,329,236
[45] Date of Patent: Jul. 12, 1994

[54] APPARATUS FOR ESTIMATING CHARGED AND POLARIZED STATES OF FUNCTIONAL GROUPS IN A SOLUTION

[75] Inventors: Nobuhiro Gemma, Yokohama; Takashi Ishino, Kawasaki, both of Japan

[73] Assignee: Kabushiki Kaisha Toshiba, Kawasaki, Japan

[21] Appl. No.: 922,787

[22] Filed: Jul. 31, 1992

[30] Foreign Application Priority Data

Jul. 31, 1991 [JP] Japan .................................. 3-191946
Feb. 7, 1992 [JP] Japan .................................. 4-022583

[51] Int. Cl.[5] ............................................ G01N 27/60
[52] U.S. Cl. ...................................................... 324/453
[58] Field of Search ............................ 324/452–456, 324/71.1, 71.4, 71.3, 663, 679, 76.49, 76.41

[56] References Cited

U.S. PATENT DOCUMENTS

| 3,753,373 | 8/1973 | Brown | 324/679 |
| 4,448,059 | 5/1984 | Kondo et al. | 324/76.49 X |
| 4,794,797 | 1/1989 | Ogawa | 324/456 |
| 4,861,990 | 8/1989 | Coley | 324/201 X |

FOREIGN PATENT DOCUMENTS

3832298 4/1989 Fed. Rep. of Germany .
2304078 10/1976 France .

OTHER PUBLICATIONS

IBM Technical Disclosure Bulletin, vol. 24, No. 10, pp. 5150–5151, Mar., 1982, D. W. Ormond, Jr., "Dielectric Defect Detector".
Journal of Vacuum Science & Technology, vol. 9, No. 2, pp. 703–706, Mar., 1991, D. W. Abraham, et al., "Lateral Dopant Profiling in Semiconductors By Force Microsccpy Using Capacitive Detection".
Science, vol. 251, S. Manne, et al., pp. 183–186, Jan. 11, 1991.
"Atomic-Resolution Electrochemistry With the Atomic Force Microscope . . . ".
Appl. Physics. Lett. 58(25), pp. 2921–2923, 1991, M. Nonnenmacher, et al., "Kevin Probe Force Microscopy."

*Primary Examiner*—Gerard R. Strecker
*Assistant Examiner*—Warren S. Edmonds
*Attorney, Agent, or Firm*—Oblon, Spivak, McClelland, Maier & Neustadt

[57] ABSTRACT

An apparatus for detecting an electrostatic force in a solution includes a sample and a cantilever. An end of the cantilever is conductive and has voltage applied to it. The apparatus detects electrostatic interaction caused by functional groups of target molecules in the solution.

12 Claims, 10 Drawing Sheets

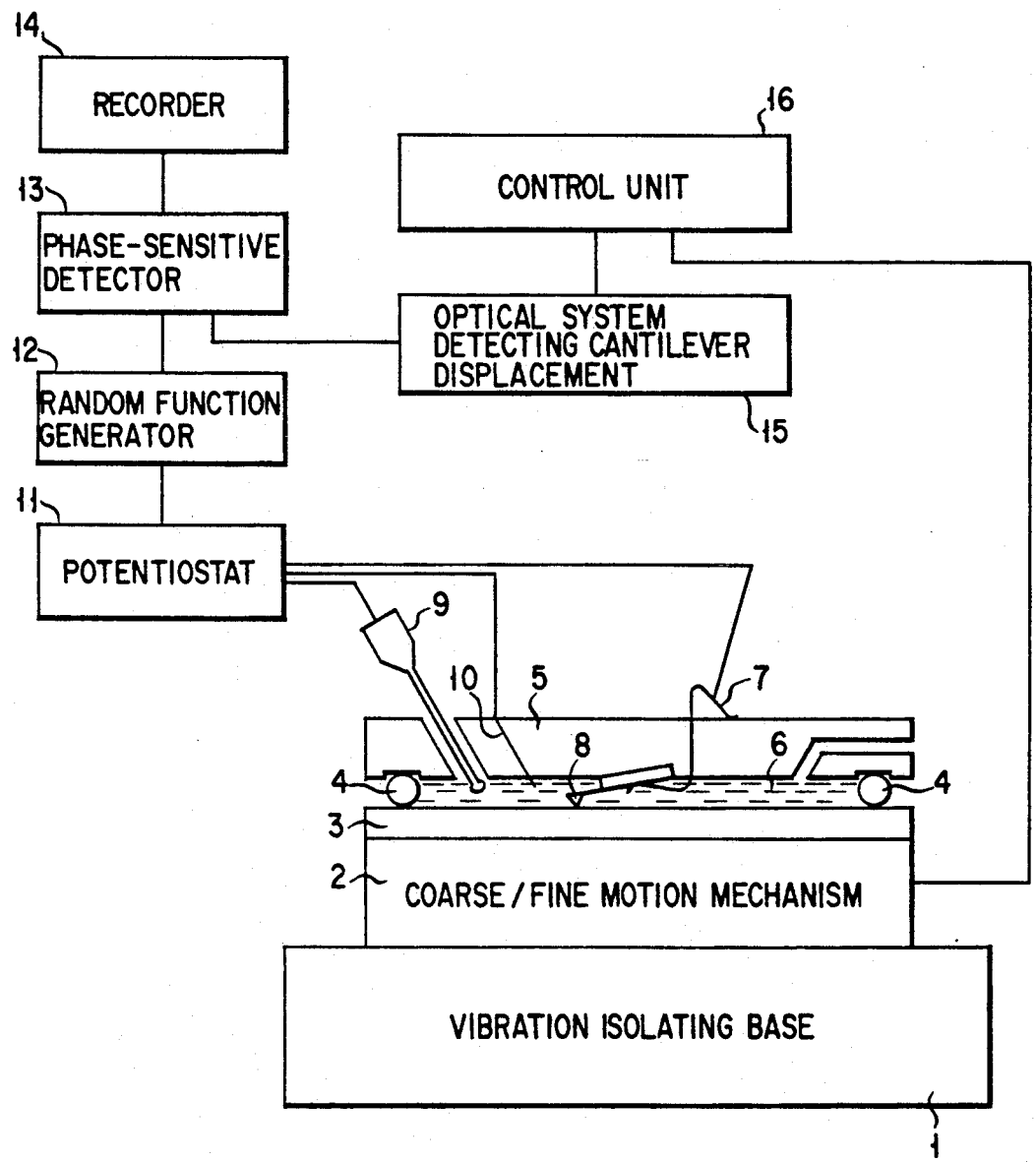
F I G. 3

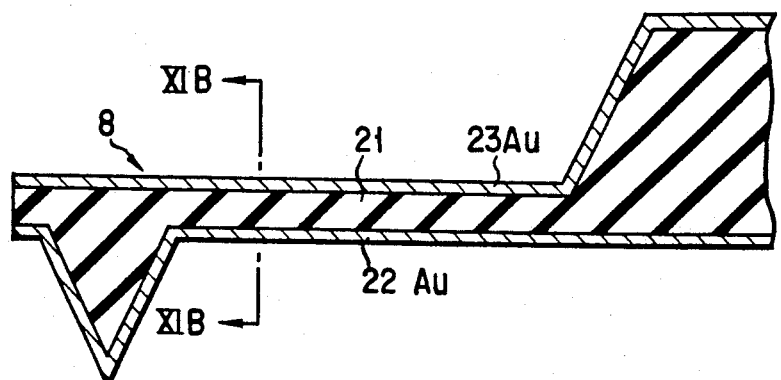
F I G. 11 A
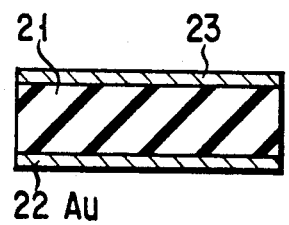
F I G. 11 B
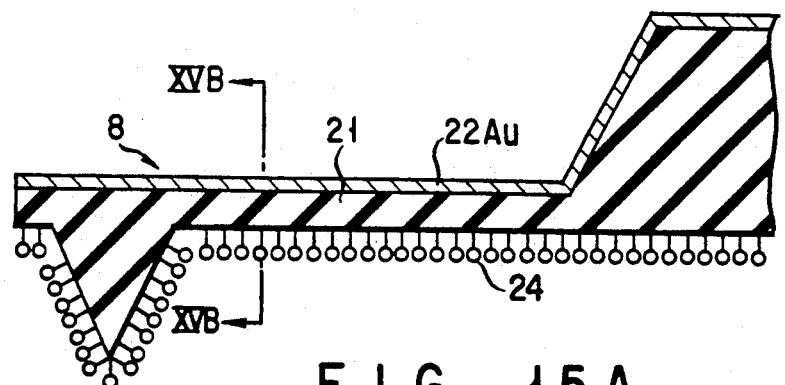
F I G. 15 A
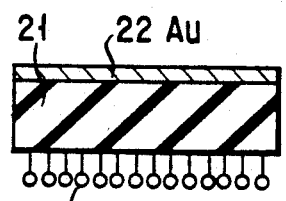
F I G. 15 B

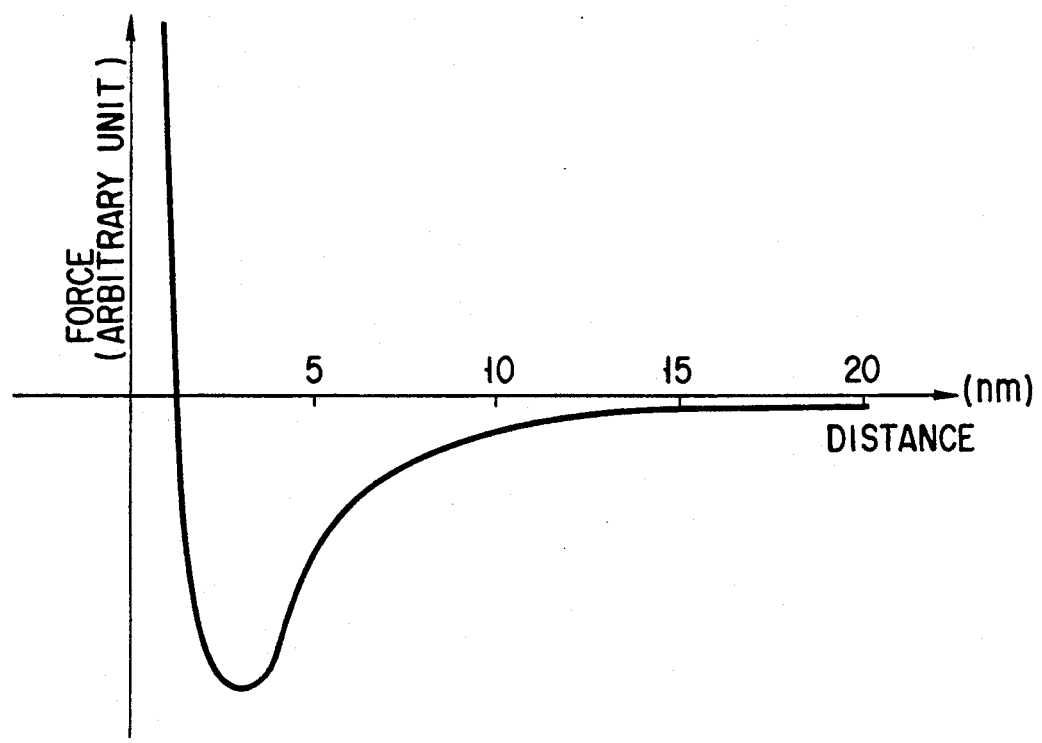
F I G. 12
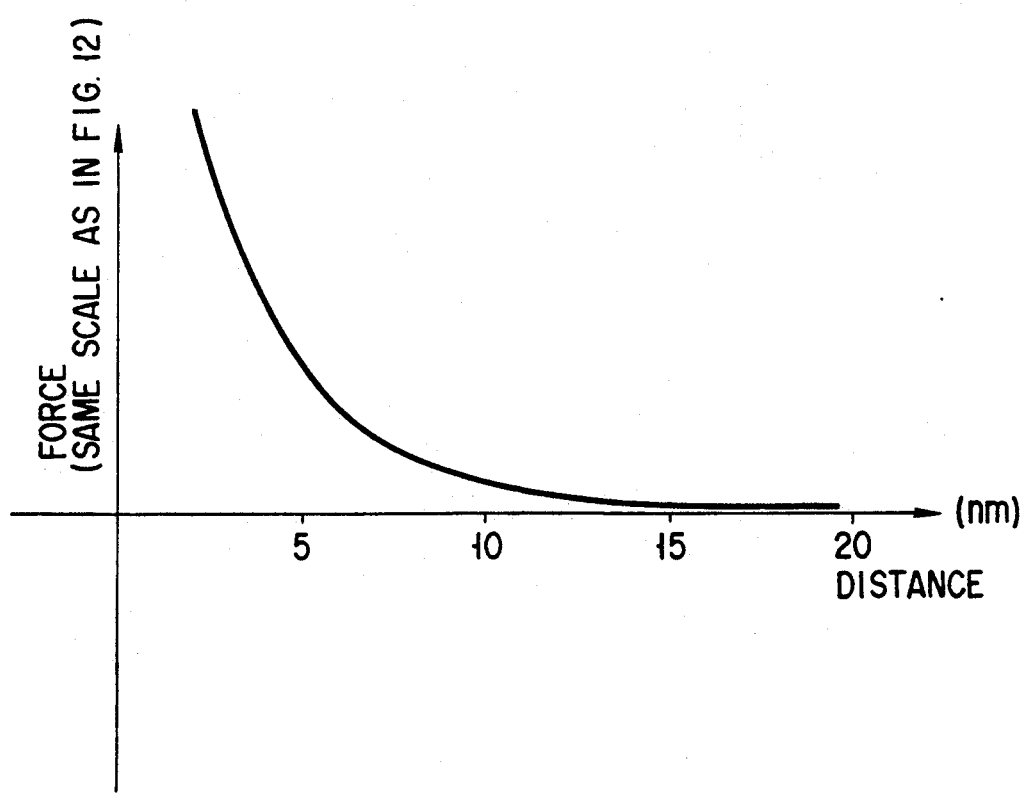
F I G. 13

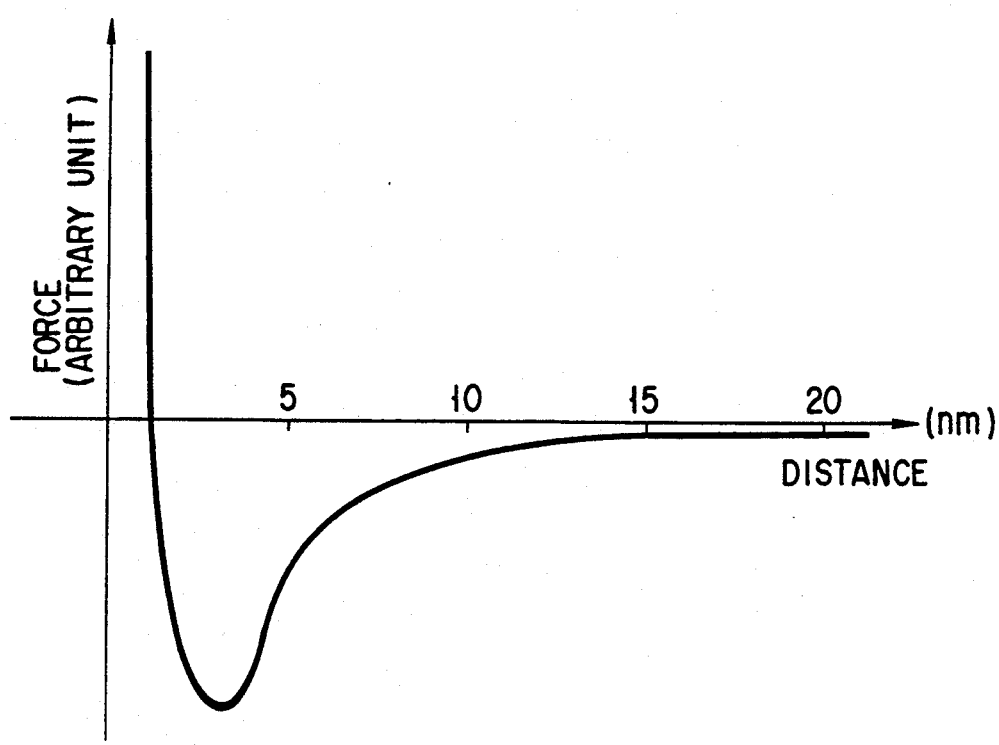
F I G. 14
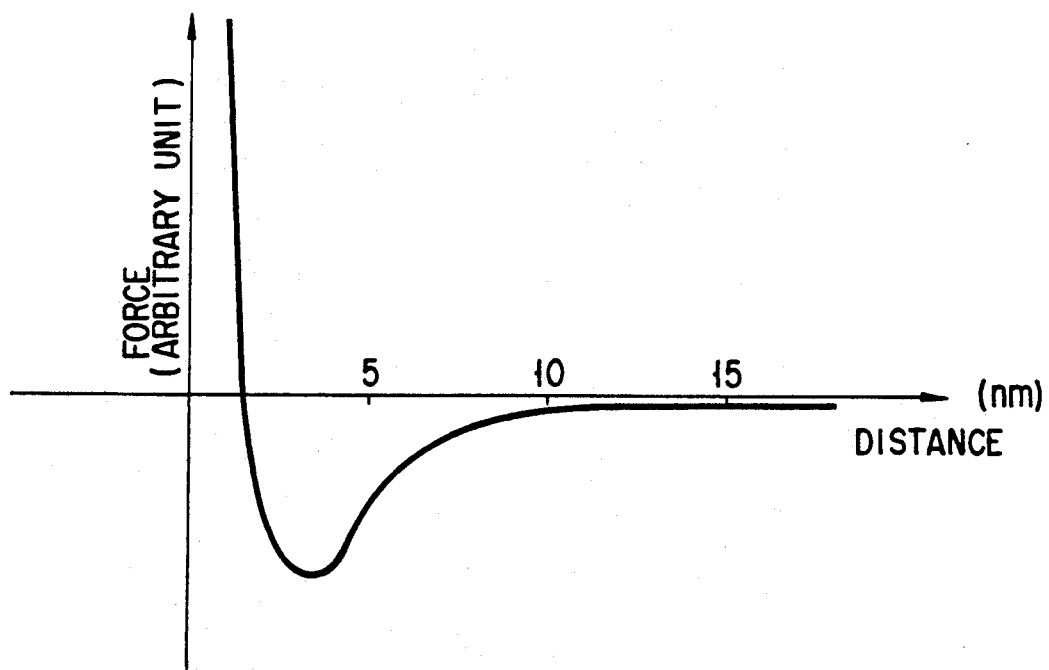
F I G. 16

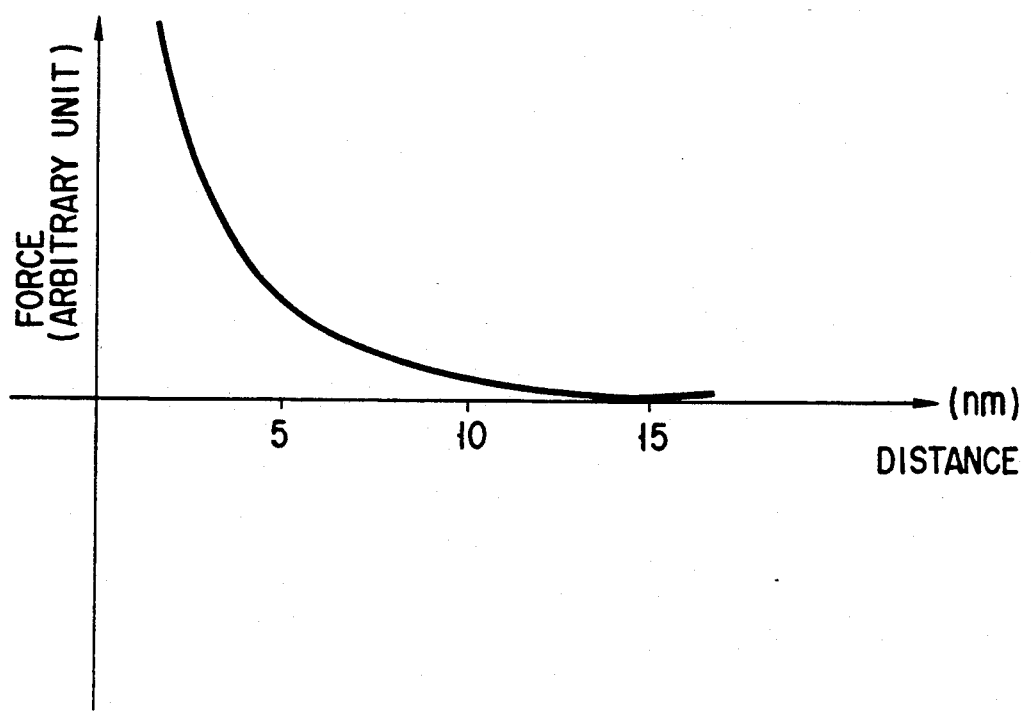
F I G. 17

APPARATUS FOR ESTIMATING CHARGED AND POLARIZED STATES OF FUNCTIONAL GROUPS IN A SOLUTION

BACKGROUND OF THE INVENTION

1. Field of the Invention

The present invention relates to an apparatus for detecting an atomic force in water, particularly an atomic force based on an electrostatic interaction.

2. Description of the Related Art

The development of a scanning tunneling microscopy (STM) has recently brought about a marked improvement in means for observing the microscopic surface structures of various types of sample surfaces. The STM is an instrument for imaging individual atoms on a sample surface one by one by monitoring tunnel currents flowing between the metal tip and the sample surface. The STM is basically used to observe metals and semiconductors having high conductivity. For samples having low conductivity, an atomic force microscopy (AFM) for detecting an atomic force acting between the tip and the sample surface is used to observe surface structures at the atomic level. Actually, the AFM is used to obtain an image of each atom on the surface of an ionic crystal such as NaCl or a lamellar substance such as mica or graphite.

Objects to be observed by the STM and the AFM are not limited to inorganic materials such as semiconductors and metals but tend to include organic molecules such as benzene and phthalocyanine and biological molecules such as proteins and DNAs. Attempts to observe the surfaces of such substances have been reported. Since there is no appropriate means for estimating the structures of biological molecules, the three-dimensional structures of many kinds of molecules are not yet known. If, therefore, surface structures can be detected by the STM and the AFM, it will greatly contributes to analysis of three-dimensional structures. In the state-of-the art techniques, however, observation of organic molecules and biological molecules by means of the STM and the AFM still entails various problems.

Organic molecular images obtained by the STM and the AFM are very obscure as compared with semiconductor and metal images which allow discrimination of the structure of each atom. Especially when a biological molecule is imaged, the overall structure image of the order of several nanometers can be only vaguely seen, but the structures of atoms cannot be discriminated from each other. In addition, reliable observation conditions are not established yet. For example, when a molecule surface is wet, an image can be obtained. If, however, the surface is dry, no image can be obtained. Furthermore, the reproducibility of images is poor.

The followings are considered as the reasons for such problems. It is basically difficult to apply the STM to samples other than those having high conductivity. Since organic molecules and biological molecules have low conductivity, theoretically, no tunnel currents should flow and no molecule images should be obtained. It therefore seems that obscure molecular structure images obtained by the STM up to the present are not attributable to tunnel currents between the tip and a molecule but are based on currents generated by some other factors. Although a definitive explanation for the generation mechanism of these currents is not yet forthcoming at present, it is highly probable that the generation of the currents is associated with thin water layers and the like which are considered to exist on molecular surfaces. Even if currents generated by such a mechanism are monitored, it is impossible to detect molecular structures at the atomic level.

Currently, the AFM is operated under the condition that a large repulsive force of $10^{-7}$ to $10^{-8}$ N acts between the tip of the cantilever and a sample. However, since an organic molecule or a biological molecule is structurally weaker than an inorganic material, if the AFM is operated under the above-mentioned condition, there is a high possibility that structural deformation or destruction of the molecule is caused. Therefore, even if an image is obtained, it is impossible to distinguish whether the image represents the inherent structure of the molecule or the structure deformed by the repulsive force.

As described above, although attempts are made to observe the structures of organic molecules and biological molecules by using the STM and the AFM, these instruments are not basically suitable for the estimation of those molecules at the atomic level. Therefore, demands have arisen for means capable of estimating molecular structures at the atomic level on the basis of the principles applicable to the physical properties of molecules.

A very distinct characteristic feature associated with the structures and physical properties of organic molecules and biological molecules is that these molecules contain functional groups, and the physical properties and functions of the molecules are greatly influenced by the bonding positions of the functional groups. Typical functional groups are —COOH, —NH$_2$, —OH, —CONH$_2$, —SH, and the like. A functional group is a minimum unit exhibiting the function of a molecule. The function of a functional group is determined by its electrical property, more specifically a charged or polarized state. For example, the group —COOH is an acidic functional group which tends to be negatively charged to become —COO$^-$ in water. The group —NH$_2$ is a basic functional group which tends to be positively charged to become —NH$_3^+$ in water. Although the groups —OH, —CONH$_2$, and —SH are not apt to be ionized in water, these functional groups themselves have large dipoles.

Since the functional groups are ionized or have large dipoles in this manner, they cause a strong electrostatic interaction with their surroundings. A typical example of such an interaction is one caused by protein. Protein consists of 20 types of amino acids. The amino acids are combined to each other to constitute a one-dimensional chain structure, and this chain structure constitutes a complicated stereoscopic structure. In water in which a protein exhibits its function, the functional groups of the amino acids being ionized or having large dipoles are exposed on the protein surface. It is considered that the charge distribution based on the functional groups is closely related to the stereoscopic structure of the protein or the molecular function inherent in the protein, typically an enzyme reaction. In spite of the fact that the charge distribution on a protein surface and the surrounding electric field distribution based on the charge distribution are important, there are no measurement means for such distributions.

A great deal of attention is paid to techniques associated with the STM and the AFM as promising candidates for means for measuring an intramolecular charge distribution based on functional groups in a solution and a surrounding electric field distribution at the atomic level. For example, electrochemical AFM (S. Manne et al., Science, 251, 183-186 (1991)), EMF (electrostatic force microscope) (B. D. Tetris et al., Phys. Rev. Lett., 63, 2669-2672 (1989); B. D. Tetris et al., J. Vac. Sci. Tech., A8(1), 374-377 (1990)), and IFM (interfacial force microscope) (S. A. Joyce et al., Rev. Sci. Instrum., 62, 710 (1991)) have been proposed. These associated techniques, however, cannot achieve the above object for the following reasons.

The electrochemical AFM is an instrument designed such that an electrode system electrochemically controlled is formed in water to observe the microscopic structure of a metal sample surface. In the electrochemical AFM, a three-electrode system is constituted in a sample cell by a metal sample as a working electrode, a stainless clip as a counter electrode which holds a cantilever, and a copper wire as a reference electrode, and the potential of the metal sample surface is controlled by the three-electrode system. Similar to the general AFM, this electrochemical AFM is designed to detect a repulsive force acting between the cantilever and a metal sample surface but cannot measure a charge distribution or a potential distribution on the sample surface. In addition, since the copper wire is used as the reference electrode, currents flow between the reference electrode and the working electrode and between the reference electrode and the counter electrode. This makes it difficult to perform accurate potential control, and various kinds of electrode reactions are caused.

The EFM is designed to measure an electrostatic force acting between a metal cantilever and a metal sample surface. The EFM, however, is designed to perform measurement in the air or in a vacuum, and does not have a cell for holding the cantilever and the sample in water. In addition, in the EFM, the cantilever is vibrated at a frequency near its resonance frequency, and the electrostatic force is detected on the basis of changes in amplitude, phase, and frequency of the vibrations. The reason why the method of vibrating the cantilever is employed is that the EFM is designed to detect a force acting in a region located 10 to 100 nm apart from the sample. In water, however, since water has a high relative dielectric constant of 80, the electrostatic force is very small in a region located 10 nm or more apart from the sample. For this reason, in water, the force must be detected in a region apart from the sample by only several nanometers. In this case, the cantilever vibration method cannot be used because the cantilever may collide with the sample. Furthermore, in the EFM, a voltage is applied between the metal cantilever and the metal sample. If this method is used in water, since water has high conductivity, a current flows in water. Consequently, various kinds of electrode reactions, e.g., the decomposition of water on the sample surface and the cantilever surface, are caused to hinder detection of the electrostatic force. Therefore, when the electrostatic force is to be detected in water, a method in which no current flows upon application of a voltage must be employed.

The IFM is an apparatus designed to measure a minute force, especially an attractive force, acting between the tip and the sample which are spaced apart by a short distance of a few nanometers or less. In an AFM of ordinary type (including an EFM and an electrochemical AFM), when an attractive force acts between the tip and the sample, the cantilever will be pulled toward the sample, causing a phenomenon known as "jump-in," and will come into contact with the sample, if the gradient of the attractive force surpasses the spring constant of the cantilever. The range over which the attractive force can be measured is inevitably limited. With the IFM it is possible to measure an attractive force built up between the tip and the sample which are spaced apart by such a short distance, without causing jump-in. This is because a capacitor is provided, one of the electrodes of which is the back surface of the cantilever, and the attractive force between these electrodes is controlled by voltage, thereby canceling out the tip-sample attractive force. An electrostatic force between the tip and the sample has not been measured in the IFM-related experiment and research hitherto reported. It is, nonetheless, possible to measure an electrostatic force in the atmosphere or in a vacuum if a metal tip is used as in the EFM. If the IFM is used in an aqueous solution, however, the attractive force acting between the electrodes of the capacitor, which are spaced apart by a few tens of microns, is screened by water and thereby decreases to so small a value that it can no longer cancel out the tip-sample attractive force. The IFM has another problem that a current flows between the electrodes of the capacitor, resulting in various electrode reactions on the electrode surfaces, which in turn render the IFM operation unstable. Hence, it is basically problematical to employ the IFM in a solution in order to evaluate intramolecular charge distribution based on functional groups.

As described above, at present, there is no appropriate means for estimating the structures of organic molecules and biological molecules at the atomic level. In spite of the fact that the functional group distribution and charge and potential distributions based on the functional groups play important roles in terms of the physical properties and functions of the molecules especially in a solution in which the molecules exhibit their functions, there is no means for measuring them. Although techniques associated with the STM and the AFM are promising as means for estimating the functional group distribution, the charge distribution, and the potential distribution, they have various kinds of problems and hence cannot achieve the above-described object.

SUMMARY OF THE INVENTION

It is an object of the present invention to provide an apparatus which can estimate charged and polarized states of functional groups in a solution and the potential distribution based on these states so as to discriminate the functional groups and identify the three-dimensional distribution of the functional groups. Especially, it is an object of the present invention to provide an apparatus which can detect only an electrostatic interaction caused by the functional group of a target molecule without being influenced by interactions from various types of ions existing in a solution. It is another object of the present invention to provide an apparatus which can detect a very small attractive force even if the distance between a tip and a sample is very short.

According to the present invention, there is provided an apparatus for detecting an electrostatic force in a solution having a sample and a cantilever placed in the solution and designed to detect a force acting between the sample and a tip on the end of the cantilever, comprising a cantilever having an end portion whose surface is made of a conductive material, means for applying a voltage to the conductive material on the cantilever end portion, and means for controlling the voltage applied to the conductive material on the cantilever end portion. It is desirable that the tip-side and back-side of the cantilever be made of conductive materials, and that the conductive materials have the same area projected onto the surface of the cantilever and be electrically connected to each other.

According to the present invention, there is provided other apparatus comprising a cantilever having conductive materials respectively formed on a tip-side surface and a back-side surface of the end of the cantilever to be insulated from each other, means for independently applying voltages to the conductive materials on the two surfaces on the end of the cantilever, and means for independently controlling the voltages applied to the conductive materials on the two surfaces on the end of the cantilever.

According to the invention, there is provided another apparatus comprising a cantilever having a distal end portion coated with polar functional groups. The polar functional groups are, for example, $-COOM_2$(M: alkali metal), $-SO_3H$, $-SH$, $-NH_2$, $-CONH_2$, $-OH$, $-COOH$, $-COOM$ (M: divalent metal), $-CO$, $-COH$, $-NO_2$, $-PO_3H$, and $-CN$. The density in which the polar functional groups are coated on the distal end portion of the cantilever is preferably $10^{14}$ $cm^{-2}$ or more. It is desirable that a conductive layer be formed on the back of the cantilever, and that the apparatus comprise means for applying a voltage to the conductive layer and means for controlling this voltage.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3 is a view showing the arrangement of an apparatus for detecting an electrostatic force according to an embodiment of the present invention;

FIG. 11A is a sectional view showing a cantilever used for the apparatus in FIG. 10;

FIG. 11B is a sectional view taken along a line XIB—XIB in FIG. 11A;

FIG. 12 is a graph showing the relationship between the sample moving distance in the vertical direction and the tip-sample attractive force, which are detected with respect to a sample consisting of a stearic acid LB film by using the apparatus in FIG. 10 under a condition of applying a voltage of $+1.2$ V to the tip-side surface of the cantilever, while controlling the voltage applied to the back-side surface of the cantilever;

FIG. 13 is a graph showing the relationship between the sample moving distance in the vertical direction and the tip-sample attractive force, which are detected with respect to a sample consisting of a stearic acid LB film by using the apparatus in FIG. 10 under a condition of applying a voltage of $-0.2$ V to the tip-side surface of the cantilever, while controlling the voltage applied to the back-side surface of the cantilever;

FIG. 14 is a graph showing the relationship between the sample moving distance in the vertical direction and the tip-sample attractive force, which are detected with respect to a sample consisting of a stearylamine LB film by using the apparatus in FIG. 10 under a condition of applying a voltage of $-0.2$ V to the tip-side surface of the cantilever, while controlling the voltage applied to the back-side surface of the cantilever;

FIG. 15A is a sectional view showing another cantilever used for the apparatus in FIG. 10;

FIG. 15B is a sectional view taken along a line XVB—XVB in FIG. 15A;

FIG. 16 is a graph showing the relationship between the sample moving distance in the vertical direction and the tip-sample attractive force, which are detected with respect to a sample consisting of a stearic acid LB film by using the apparatus in FIG. 10 and the cantilever in FIG. 15, while controlling the voltage applied to the back-side surface of the cantilever;

FIG. 17 is a graph showing the relationship between the sample moving distance in the vertical direction and the tip-sample attractive force, which are detected with respect to a sample consisting of a stearylamine LB film by using the apparatus in FIG. 10 and the cantilever in FIG. 15, while controlling the voltage applied to the back-side surface of the cantilever.

DETAILED DESCRIPTION OF THE PREFERRED EMBODIMENTS

Figure 1A:
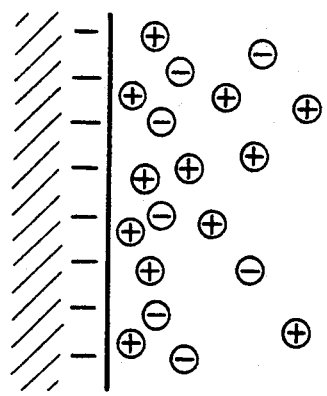
FIG. 1A is a view for explaining the distribution of ions in a solution upon application of a voltage to a cantilever.

The present invention will be described in detail below.

The first object of this invention is to provide an apparatus which can identify a functional group existing on the surface of a sample in water. Functional groups greatly differ from each other in electrical properties, more precisely in charged state and polarized state. For example, —COOH is negatively charged in water, becoming —COO$^-$. Conversely, —NH$_2$ is positively charged in water, becoming —NH$_3^+$. A functional group, thus ionized, attracts an ion of the opposite polarity existing in the water, whereby an electric double layer is formed around the functional group.

In the present invention, the surface of the end portion, more precisely the tip, of a cantilever is made of conductive material, and the voltage applied to the conductive material is controlled externally, thereby detecting the electrostatic force built up between the tip and a functional group and identifying the functional group based on the behavior of the electrostatic force. When a voltage is applied to the tip made of the conductive material, charges are accumulated in the surface of the tip. As a result, the ions in the water are attracted, forming an electric double layer around the tip, in the same way around the functional group. To be more specific, when a positive voltage is applied to the tip, the negative ions in the water gather in the vicinity of the surface of the tip, forming an electric double layer. When a negative voltage is applied to the tip, the positive ions in the water gather, forming an electric double layer. In either case, an electrostatic force acts between the tip made of the conductive material and the functional group.

In the case where a positively charged functional group, e.g., —NH$_3^+$, and a tip which is applied an positive voltage, two electric double layers are formed around the tip and the functional group, respectively, each having many negative ions distributed in it. The thickness of each electric double layer depends on the concentration of the ions existing in the water. It is about 100 nm when the ion concentration is $10^{-5}$ mol/l; about 10 nm when the ion concentration is $10^{-3}$ mol/l; and about 1 nm when the ion concentration is $10^{-1}$ mol/l. When the tip and the functional group are moved closer to each other, an electrostatic force starts acting between them at a point where the electric double layers overlap. A repulsive force acts between —NH$_3^+$ and the positively biased tip. The repulsive force increases as the distance between them decreases. When the distance between them further decreases to about a tenth the thickness of the electric double layer, the electrostatic force acting directly between the charge at the tip surface and the functional group becomes dominant. The electrostatic force directly acting between —NH$_3^+$ and the positively biased tip is also a repulsive force, the magnitude of which is about $10^{-9}$ N. As for an electrostatic force between —NH$_3^+$ and the tip which is applied a negative voltage, an attractive force starts acting at a point where the electric double layers overlap. This electrostatic attractive force directly acting between the tip and the functional group, also have a magnitude of about $10^{-9}$ N.

In the case of a functional group of —COO$^-$ having a negative charge, an attractive force acts between the group and the tip if a positive voltage is applied to the tip, and a repulsive force acts between the group and the tip if a negative voltage is applied to the tip.

In the case where a functional group, such as —CONH$_2$, —OH, or —SH, is not ionized, no electrostatic force acts due to overlapping of the electric double layers. However, the electrostatic force, which directly acts between the tip and the functional group when they are very close to each other, depends on the large dipole of the functional group. As for such an electrostatic force, whether an electrostatic force acts as an attractive force or a repulsive force and the polarity of a voltage to be applied are determined by the atomic charge of an atom, of a functional group, located closest to the tip. For example, in —CONH$_2$, an H atom and an O atom respectively have positive and negative charges. Therefore, in a case where an H atom is located closest to the tip, if the cantilever voltage is positive, a repulsive force acts, whereas if the voltage is negative, an attractive force acts. In contrast to this, in a case where an O atom is located closest to the tip, if the cantilever voltage is positive, an attractive force acts, and vice versa. Since the magnitude of the force is determined by the magnitude of an atomic charge, the force varies in magnitude even with similar dipole-type functional groups.

In addition, whether a functional group becomes ionized state or neutral polarized state depends on the pH value of a solution. Therefore, the magnitude, the voltage dependence, and the distance dependence of an electrostatic force near the functional group can be changed by changing the pH value.

As described above, since the characteristics of an electrostatic force greatly vary depending on the type of a functional group, the functional group located closest to the tip can be identified by measuring the electrostatic force. Therefore, with respect to a molecule whose three-dimensional functional group distribution is not known, such as a protein, the distribution of functional groups located on the molecule surface can be estimated by scanning the cantilever near the molecule.

As a cantilever in the present invention of which end portion is made of a conductive material, a cantilever made of a conductive material, or a cantilever consisting of a base member made of an insulating material such as SiN or SiO$_2$ and a conductive film coated on the surface of the base member may be used. A preferable conductive material is one whose surface is resistant to oxidation. For example, noble metals such as Au, Pt, Rh, and Pd can be used. In addition, it is preferable that a conductive film uniformly formed on the surface of the base member have a thickness of 10 nm or more in order to allow a stable operation of the cantilever in a solution upon application of a voltage thereto.

According to the principle of the present invention, no problems are posed in measurement of an electrostatic force regardless of whether a means for applying a voltage to the conductive material on the end portion of the cantilever is a DC power supply or an AC power supply. However, in order to efficiently identify a functional group, it is preferable to apply an AC voltage and to use a means for synchronously detecting the AC voltage and a cantilever displacement. For example, a phase-sensitive detection method using a lock-in amplifier or the like is preferable. If such a means is used, a considerably small electrostatic force can be measured, since an S/N ratio is increased. In addition, the functional group can be quickly identified, since the charge amount of a functional group can be determined on the basis of a change in electrostatic force with respect to the voltage.

In the present invention, as a means for controlling a voltage applied to the conductive material on the end portion of the cantilever, a reference electrode such as a hydrogen electrode, a calomel electrode, a silver/silver chloride electrode, a mercury/mercury oxide electrode, or a mercury/mercury sulfate electrode is preferably used. The use of such a reference electrode can greatly reduce the amount of current flowing in water. Consequently, the cantilever potential can be stabilized, and electrode reactions at the surface of the end portion of the cantilever can be prevented, thus allowing stable measurement of an electrostatic force.

As an electrode system, a two-electrode system constituted by a cantilever and a reference electrode may be used. Alternatively, a counter electrode may be additionally arranged to form a three-electrode system constituted by the cantilever, the reference electrode, and the counter electrode. The three-electrode system is more suitable for the object of the present invention than the two-electrode system because it can perform high-precision potential control by using a potentiostat and can estimate the cantilever surface by measuring a current-voltage curve, a so-called cyclic voltammogram.

According to this invention, to detect the electrostatic force between the tip and the functional group, a second method may be used in which the surface of the tip on the end portion of the cantilever is covered with a functional group, e.g., $-NH_2$. If $-NH_2$ exists on the surface of the sample, both the tip and the sample have ionized $-NH_{3+}$ in their surfaces, and an electrostatic repulsive force starts acting between them at a point where the electric double layers surrounding the tip and the sample, respectively, come to overlap each other. If $-COOH$ exists on the surface of the sample, an attractive force starts acting between them due to the electrostatic interaction of $-COO^-$ and $NH_3^+$ at a point where the electric double layers come to overlap each other. Even when the functional group in the surface of the sample is not ionized, whether the electrostatic force is an attractive force or a repulsive force, and whether it is large or small are determined depending on the atomic charge of the atom nearest to the tip in the functional group, as in the case where the tip is made of conductive material.

Since the electrostatic interaction between the tip and the sample greatly depends on the functional group existing in the surface of the sample even when the tip is covered with a functional group, the functional group in the surface of the sample can be identified by measuring the electrostatic force.

The following three methods are available for covering the tip of the cantilever with a polar functional group.

The first is LB method. In this method, a silane coupling agent having methyl groups, such as hexamethyldisilazane, is adsorbed to the surface of a commercially available cantilever made of SiN in vapor phase, thereby rendering the surface thereof hydrophobic. Next, an LB molecule having a hydrophobic group and a polar functional group at the ends, respectively, is applied to the cantilever, forming a monomolecular film thereon, with the hydrophobic group contacting the surface of the cantilever which is now hydrophobic.

A typical example of an LB molecule is one having the structure of $CH_3(CH_2)_nX$, where n is 16 to 22, X is $-COOM_2$ (M: alkali metal), $-SO_3H$, $-SH$, $-NH_2$, $-COHN_2$, $-OH$, $-COOH$, $-COOM$ (M: divalent metal), $-CO$, $-COH$, $-NO_2$, $-PO_3H$, $-CN$, or the like.

The second method is one in which bonding of Au and thiol group ($-SH$) is utilized. In this method, the cantilever is covered with Au by means of either vapor deposition or sputtering. Next, the Au-covered cantilever is immersed in a solution containing molecules each having a thiol group and a polar functional group at the ends, respectively, and is left to stand for about one day at room temperature. Bonding of Au and thiol group is thereby accomplished, and the surface of the cantilever is covered with the polar functional group. In the second method, a molecule having the structure of $HS(CH_2)n\ X$ is used, where n is 10 to 20 and X is typically $-CH_2OH$, $-CN$ or $-COOH$. Instead, X can be $-NH_2$, $-CONH_2$, $-OH$, $-SO_3H$, $-PO_3H$, or the like.

The third method is one in which the surface of a cantilever made of Si, SiN or $SiO_2$ is treated with acid, thereby exposing $-OH$ group, and a silane compound is adsorbed to the surface of the cantilever. The silane compound used is one represented by $YRSiX_3$, where X is a group bonded to a silicon atom and being hydrolytic, such as $-OR$, $-Cl$ or $-NR_2$, Y is a polar functional group, such as $-HN_2$, $-NHCH_2CH_2NH_2$, $-SH$ or $-Cl$. The adsorption is performed in vapor phase or in a solution of the silane compound. The polar functional group Y appears on the surface of the cantilever in both cases.

Two methods of detecting the electrostatic force between the tip and the functional group have been described. In the first method, a tip at the end portion of the cantilever is made of conductive material and a controlled voltage is applied to this tip. In the second method, the tip at the end portion of the cantilever is covered with a polar functional group. As for the first method, there is a problem to be taken in consideration. When a voltage is applied to the tip made of conductive material, the cantilever is displaced due to the electrostatic interaction between the ions existing in water and the cantilever. Detection of the force acting between the tip and the surface of the sample will be hindered by this phenomenon.

Accordingly, the second object of this invention is to provide means for preventing the cantilever from moving, despite the electrostatic interaction between the tip and the ions existing in the water.

The electrostatic interaction between the ions in the water and a cantilever consisting of a base member made of insulating material and a conductive film formed on the tip-side surface thereof will now be discussed.

Figure 1B:
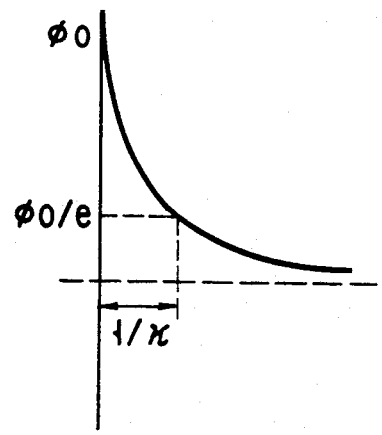
FIG. 1B is a graph showing the relationship between the distance from a cantilever surface and the potential.

When a voltage is applied to the conductive film on the cantilever surface in a solution, ions in the solution are unevenly distributed near the cantilever surface, as shown in FIG. 1A. As a result, a large force acts on the cantilever because of an electrostatic interaction from the ions. The magnitude of the force acting on the cantilever at this time can be estimated by a simple model. According to a model of a diffused double layer by Gouy-Chapmann (L. Gouy: J. Phys., (4), 9, 457 (1910); L. Gouy: Ann. Phys., (9), 7, 129 (1917); D. L. Chapmann: Phil. Mag., (6), 25, 475 (1913)), the potential changes as shown in FIG. 1B. In this case, a potential $\phi(x)$ at a point spaced apart from the cantilever surface in the vertical direction by a distance x can be given by:

$$\phi(x) = \frac{2KT}{Ze} \ln \frac{1 + \psi\exp(-\kappa x)}{1 - \psi\exp(-\kappa x)}$$

where k is Boltzmann's constant, T is temperature of a solution, Z is a valence of ions in a solution, and e is elemental charge.

Note that $\psi$ and $\kappa$ are defined as follows:

$$\psi = \frac{\exp(Ze\phi_0/2kT) - 1}{\exp(Ze\phi_0/2kT) + 1}$$

where $\phi_0$ is potential of cantilever in a solution.

$$\kappa^2 = \frac{8\pi n Z^2 e^2}{\epsilon_W kT}$$

where n is ion density in a solution, and $\epsilon_W$ is dielectric constant of water.

In equation 2, $1/\kappa$ represents the thickness of an electric double layer. In this case, an electric field strength En in the vertical direction with respect to the cantilever surface is given by:

$$En = \frac{4KT}{Ze} \cdot \frac{\kappa\psi}{1 - \psi^2}$$

The magnitude of a force acting on a conductor in a constant electric field can be represented by $fn = \epsilon_W En^2/2$ per unit area. Assume that the temperature of a solution is equal to room temperature, and that the solution is a KCl solution of $10^{-5}$ (mol/l). When $Z=1$ and $\epsilon_W = 6.955 \times 10^{-10}$ (F/m), $1/\kappa$ becomes $10^{-7}$ (m). If $m0=0.1$ (V), En becomes $1.76 \times 10^6$ (V/m). If the area of the cantilever surface $S=3.33 \times 10^{-9}$ (m²), a magnitude of a force Fn acting in a direction perpendicular to the cantilever surface is given as follows: $Fn = fnS = \epsilon_W En^2 S/2 = 3.65 \times 10^{-6}$ (N) = 3.65 ($\mu$N). The magnitude of this force is proportional to the molar concentration of the solution. At the concentration of $10^{-3}$ (mol/l), $Fn = 3.65 \times 10^2$ ($\mu$N). At the concentration of $10^{-1}$ (mol/l), $Fn = 3.65 \times 10^4$ ($\mu$N).

Therefore, as for the cantilever in which the conductive film is formed only on the tip-side surface of the insulating cantilever base member, a large force of several micronewton or more due to an electrostatic interaction with ions in water acts only on the tip-side surface. In this case, the cantilever is displaced by several micrometers or more. As a result, it is very difficult to detect a charge distribution on the sample surface.

In the present invention, in order to prevent the cantilever displacement due to an electrostatic interaction with ions in water, a cantilever consisting of a base member and conductive films formed on the two sides thereof which are connected with each other. In this case, the potentials of the two surfaces in the solution are equal to each other, or ions near the two surfaces are equal in type, concentration, and distribution.

Figure 2:
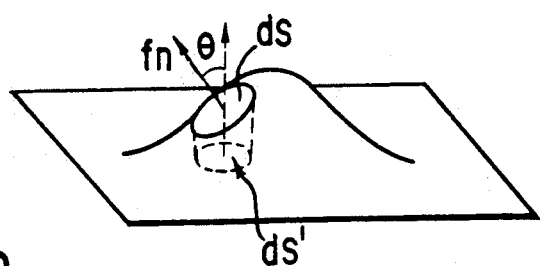
FIG. 2 is a view for explaining the influence of an interaction due to ions in the solution, which act on two surfaces, having different shapes, of the cantilever.

Note that since a tip is formed on one of the surfaces of the cantilever, the two surfaces have different shapes. However, as will be described below, forces acting on the two surfaces of the cantilever are the same. Only forces acting in directions perpendicular to the surfaces of the cantilever will be considered here. Assume two very small areas, i.e., a very small area dS of a surface forming an angle i with respect to the cantilever surface, and a very small area dS' obtained by projecting the area dS to the cantilever surface, as shown in FIG. 2. If the charge density on a surface is constant, the electric field strength perpendicular to the surface is constant. Therefore, a force fn per unit area, which acts perpendicular to the very small area dS, is also constant. Here a force acting on the vary small area dS is given by $fndS \times \cos\theta$. On the other hand, a force acting on the very small area dS' is represented by $fndS'$. It is apparent since $dS' = dS \times \cos\theta$ that the two forces are equal to each other. That is, when projected areas of the conductive films on the two sides are equal, equal forces act on the two surfaces of the cantilever even if a tip or other minute recesses and projections are formed on one surface. According to the above-described cantilever designed such that both tip-side and back-side surfaces are made of a conductive material, and the two surfaces are electrically connected to each other, forces acting on the two surfaces of the cantilever, due to interactions with various types of ions existing in the solution, cancel each other. Therefore, when the cantilever having such a structure is used, only an electrostatic interaction attributable to a functional group existing on a sample surface can be detected with almost no influence of an electrostatic interaction with ions in the solution.

No matter whether both surfaces of the cantilever base member are covered with the same electrically conductive material or the different conductive materials, the potentials of these surfaces are equal, provided the surfaces are electrically connected. Thus, the interaction due to the ions in the water will be canceled at the both surfaces of the cantilever.

The constitution of such a cantilever will be described in more detail below. An example is one that Cr and Au films are sequentially formed on the two surfaces of the insulating cantilever by vacuum deposition. In this case, in order to easily ensure electrical conduction between the two surfaces, it is preferable that each surface of the cantilever be inclined at 10 to 30 degrees with respect to a deposition source to coat a conductive material on its side surface. In order to ensure the symmetry of the films formed on the respective side surfaces of the cantilever, the cantilever is preferably rotated. In addition, in order to prevent thermal deformation of the cantilever, a conductive material such as Au, Pt, Rh, Pt-Pd, or Au-Pd may be coated on the two surfaces of the cantilever by sputtering in a vacuum instead of vacuum deposition. Furthermore, a conductive material such as a silver paste may be coated on side surfaces of a supported end portion of the cantilever so as to ensure electrical conduction between the two surfaces. Similarly, the two surfaces of the cantilever may be connected to each other through metal wires or the like.

The third object of the present invention is to provide an apparatus which can detect a detailed characteristic of an attractive force even if the distance between a tip and a sample is very small with preventing "jump-in" phenomenon. When the tip and the sample surface are moved closer to each other in a solution, the cantilever may be pulled toward the sample at a point where the gradient of the attractive force between the tip and the sample surface exceeds the spring constant of the cantilever. This is "jump-in" phenomenon. For example, in measurement using a commercially available cantilever having a spring constant k=0.58 N/m and a tip end having a curvature radius of about 100 nm, "jump-in" occurs at a position where the tip end is located several nanometers to several tens of nanometers apart from a sample surface, so that it is impossible to detect a detailed characteristic of a very small attractive force at a position closer to the sample surface.

It is true that data about the charged state of the functional group can be acquired to identify the functional group, by checking what a distance the jump-in is caused, how much the cantilever is displaced due to the jump-in, or what an applied voltage the jump-in is caused in the case of a cantilever made of conductive material. In order to analyze the characteristic of the attractive force in greater detail, however, it is required that the jump-in be suppressed.

To achieve this object in the present invention, a cantilever consisting of a insulating base member and conductive films formed on the two surfaces of the base member which are insulated from each other is used, and controlled voltages are independently applied to the conductive films on the two surfaces.

The behavior of the cantilever having such a structure in a solution will be described bellow. In this structure, if a lead is connected to only the conductive film on one surface, the potential of the surface to which the lead is connected is different from that of the opposite surface in the solution, and ions near the two surfaces differ in type, concentration, and distribution. More specifically, near the surface to which the lead is connected, the amount of charge induced on the surface varies in accordance with the applied voltage, resulting in change of the type, concentration, and distribution of ions in the solution. In contrast to this, near the opposite surface, the potential in the solution is kept constant, and the charge slightly moves because of the difference in chemical potential between water molecules and the conductive material to form a natural potential. For this reason, the potentials of the two surfaces of the cantilever cannot be set to be equal to each other. Therefore, when a voltage is applied to the cantilever, the ions in the solution are unevenly distributed only near the surface to which the lead is connected. As a result, a large force of several micronewton or more is applied to the cantilever, similar to the above case.

On the other hand, the case where leads are connected to the conductive films on both surfaces is considered bellow. When the tip end and the sample surface are sufficiently spaced apart from each other, if equal voltages are applied to the two surfaces of the cantilever, forces acting on the two surfaces due to interactions with various types of ions existing in the solution are canceled to each other.

If the tip end is moved closer toward the sample in this state, an electrostatic interaction is caused between charges induced near the tip end by the voltages applied to the cantilever and charge existing near the sample surface. Assume that an attractive force based on the electrostatic interaction acts between the tip and the sample surface. In this case, if a voltage is further applied to only the back-side surface of the cantilever, the magnitude of the attractive force based on the electrostatic interaction with ions in the solution can be controlled on the back-side surface. Since the displacement of the cantilever can be kept constant by balancing an attractive force acting on the back-side surface of the cantilever against a very small attractive force acting between the tip and the sample surface, the phenomenon of "jump-in" can be prevented. In addition, the small attractive force acting between the tip and the sample surface can be calculated from the difference between voltages applied to the two surfaces of the cantilever required to keep the displacement of the cantilever constant. In contrast to this, if a repulsive force based on an electrostatic interaction acts between the tip and the sample surface, the magnitude of the repulsive force can be estimated by further applying a voltage to only the tip-side surface of the cantilever, similar to the case of an attractive force.

As for a cantilever consisting of an insulating base member and functional groups which cover the tip-side surface of base member, the back-side surface is additionally covered with a conductive film, and a means for applying a voltage to the conductive film and a means for controlling the voltage are arranged. Also in this case, by changing the magnitude of a voltage applied to the conductive film, the magnitude of an attractive force acting on the back-side surface of the cantilever can be freely controlled. The displacement of the cantilever can be kept constant by controlling the magnitude of an attractive force acting on the backside surface of the cantilever to balance against a very small attractive force acting between the tip and the sample surface. Therefore, the attractive force between the tip and the sample can be calculated from the voltage applied to the conductive film required to keep the displacement of the cantilever constant. In this manner, even in the case where a tip and a sample surface are located at a very short distance, the magnitude of a very small attractive force acting between them can be estimated without causing the "jump-in" phenomenon.

In this invention, when the end portion of the cantilever is covered with a conductive film, it is preferable to apply an AC voltage to the conductive film as above-described. In this case, an upper limit of the frequency of the AC voltage is preferably set in accordance with the type and concentration of a solution and the magnitude of the voltage. The frequency of the AC voltage will discussed in more detail below.

When no voltage is applied to the cantilever, ions in the solution are almost evenly distributed near the cantilever surface. If a voltage of a predetermined magnitude is applied to the cantilever in this state, various types of ions in the solution move in accordance with the potential difference between the cantilever surface and the solution. After a lapse of a sufficient period of time, the distribution of the ions in the solution reaches an equilibrium state, and an electric double layer is formed near the cantilever surface, as described above.

If a constant voltage is continuously applied to a conductor in a solution from a certain time (t=0), the distribution of charge density near the conductor surface can be represented as follows (A. J. Bard and L. R. Faulkner: "Electrochemical Method" p. 144):

$$\rho(x,t) = nZ\left\{1 - 2erf\left(\frac{x}{2D^{1/2}t^{1/2}}\right)\right\}$$

$$erf(x) = \frac{2}{\pi^{1/2}} \int_o^x e^{-y^2} dy$$

Assume that $\phi_0 < 0$, and that only ions having negative charges are uniformly distributed near the conductor surface before the voltage is applied. In this case, for the sake of simplicity, assume that one type of positive ions and one type of negative ions of an electrolyte exist in a solution, and that the positive and negative ions are equal in concentration, valence, and diffusion constant.

The distribution of ions near the conductor surface in an equilibrium state can be given as follows (L. Gouy: J. Phys., (4), 9, 457 (1910); L. Gouy: Ann. Phys., (9), 7, 129 (1917); D. L. Chapmann: Phil. Mag., (6), 25, 475 (1913)):

$$\rho_{eq}(x) = -\epsilon \kappa^2 \phi_0 exp(-\kappa x)$$

If $\rho(d, g) = \rho eq(d)$, a time g required to form an electric double layer at a point spaced apart from the conductor surface by $x = d$ can be estimated. Qualitatively, $\tau$ decreases with an increase in n or D, and $\tau$ increases with an increase in z, $\phi_0$ or d. In order to allow ions on the cantilever surface to sufficiently respond, a frequency f of an AC voltage applied to the cantilever must be set to satisfy a condition of $f \leq 1/\tau$.

In this case, if $x = d < < 2D^{\frac{1}{2}}\tau^{\frac{1}{2}}$, since $erf(x) \sim (2/\pi^{\frac{1}{2}})x$, the following equations can be established:

$$nZ\left(1 - \frac{2d}{\pi^{1/2}D^{1/2}t^{1/2}}\right) = -\epsilon\kappa^2\phi_0 exp(-\kappa x)$$

$$\tau = \frac{4d^2}{\pi D}\left\{1 + \frac{\epsilon\kappa^2 \phi 0}{nZ} \cdot exp(-\kappa x)\right\}^{-2}$$

$$f \leq \frac{\pi D}{4d^2}\left\{1 + \frac{\epsilon\kappa^2 \phi 0}{nZ} \cdot exp(-\kappa x)\right\}^{2}$$

The value of $\tau$ is actually obtained as follows. Assume that $D = 2.0 \times 10^{-9} (m^2/s)$, $n = 10^{-5} (mol/l)$, $Z = 1$, $\phi_0 = 10$ mV, and $d = 10$ nm. In this case, when $e = 1.6 \times 10^{-9}$, $\epsilon = 6.9 \times 10^{-10}$ (F/m), $1.4 \times 10^{-23}$ (J/k), $T = 300$ (k) are substituted into the corresponding equation, $\tau = 4.9 \times 10^{-7}$ (s) is obtained. In this case, $f \leq 2.0 \times 10^6$ (Hz).

Embodiments of the present invention will be described below with reference to the accompanying drawings.

FIG. 3 shows the arrangement of an apparatus for detecting an electrostatic force in a solution according to an embodiment of the present invention. FIG. 4 is a sectional view of a cantilever constituting this apparatus. As shown in FIG. 3, a coarse/fine motion mechanism 2 is mounted on a vibration isolating bed 1. A sample 3 is placed on the coarse/fine motion mechanism 2. The sample 3 is vertically and horizontally moved by the coarse/fine motion mechanism 2. A cantilever holder 5 is placed on the sample 3 through an O-ring 4 to form a measurement cell between the sample 3 and the cantilever holder 5. While the sample B is moved in the vertical direction, it compresses the O-ring 4. Therefore, the O-ring 4 is preferably made of a material having a high compressibility. In this embodiment, the O-ring 4 consists of a silicone-based resin. An aqueous solution 6 is stored in the measurement cell. A cantilever 8 is fixed to the lower surface of the cantilever holder 5 with a fixing clip 7 formed by coating the entire surface of a stainless base member with Au. Since the clip 7 is dipped in the solution, it is preferably made of a noble metal so as not to adversely affect potential measurement.

Figure 4A:
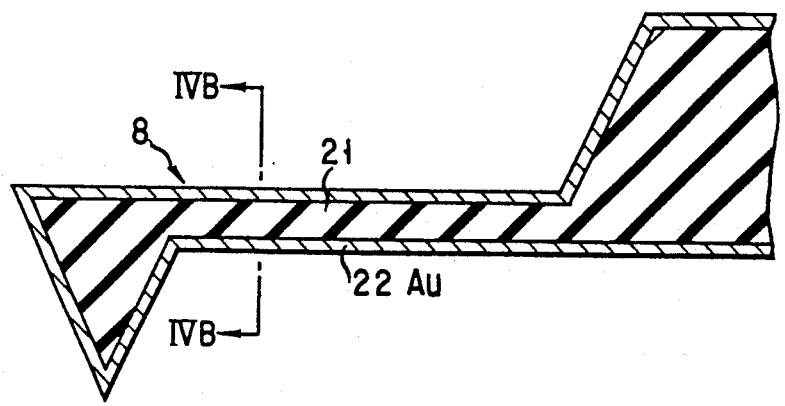
FIG. 4A is a sectional view showing a cantilever used for the apparatus in FIG. 3.
Figure 4B:
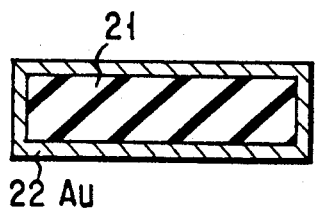
FIG. 4B is a sectional view taken along a line IVB—IVB in FIG. 4A.

As the cantilever 8, for example, the cantilever shown in FIGS. 4A and 4B is used. A base member 21 of this cantilever is made of $Si_3N_4$, and has a tip in the form of a quadrangular cone on its end. A 100-nm thick Au film 22 is formed on the two surfaces of the base member 21 by vapor deposition.

A reference electrode 9 and a counter electrode 10 are dipped in the solution 6 in the measurement cell. As the reference electrode 9, a calomel electrode or a silver/silver chloride electrode is used. As the counter electrode 10, a Pt wire is used.

The clip 7 and the reference electrode 9 are connected to a voltage application system constituted by a potentiostat 11 and a function generator 12. With this arrangement, a voltage can be applied to the Au film 22 on the surface of the cantilever 8 while it is controlled. The displacement of the cantilever 8 is detected as a photodiode output by an optical system 15 for detecting cantilever displacement constituted by a semiconductor laser, a mirror, a lens, and a photodiode. More specifically, a laser beam is irradiated on the back-side surface of the cantilever 8, and the reflected light is detected by the photodiode so that the displacement of the cantilever 8 is detected as a change in photodiode output. When an AC voltage is applied to the cantilever 8, the voltage and the displacement of the cantilever 8 are synchronously detected by a phase-sensitive detector 13 and are recorded on a recorder 14. When a DC voltage is applied to the cantilever 8, the voltage is directly applied to the cantilever 8 through an internal power supply within the potentiostat 11. In this case, the applied voltage and the displacement of the cantilever 8 are directly recorded on a recorder 14. The coarse/fine motion mechanism 2 is controlled by a control unit 16.

EXPERIMENT 1

Only the tip-side surface of an $Si_3N_4$ base member was coated with Au by sputtering to manufacture a cantilever (comparative example). In contrast to this, the two surfaces of an $Si_3N_4$ base member were coated with Au by sputtering to manufacture a cantilever as shown in FIG. 4 (embodiment). Each of the cantilevers had a spring constant $k = 0.58$ N/m.

Each cantilever was immersed in an aqueous KCl solution of $10^{-5}$ (mol/l), and the distance between the tip end of the cantilever and a sample surface was set to be about 100 $\mu m$. A voltage of $-50$ mV to $+100$ mV was applied to the cantilever by using the potentiostat and the function generator to measure the displacement of the cantilever.

When the cantilever of the comparative example was used, the maximum displacement was about 200 nm. The magnitude of the force was estimated to be about 0.1 $\mu N$ on the basis of the spring constant. When the cantilever of the embodiment was used, the maximum displacement was about 0.1 nm. The magnitude of this force was about 0.05 nN, which was 1/2000 to that in the case of the comparative cantilever. It is clear from this experimental result that the use of the cantilever of the embodiment can reduce an interaction with ions in the solution.

In Experiments 2 to 4, which will be described below, the use is made of the cantilever 8 as shown in FIG. 4, manufactured by forming 100-nm thick Au films on the two surfaces of an $Si_3N_4$ base member by vapor deposition, which are connected to each other.

EXPERIMENT 2

A 200-nm thick $SiO_2$ film was formed on an Si substrate by thermal oxidation. After the resultant substrate was left in a hexamethyldisilazane gas for 24 hours, it was baked at 100° C. to form an adsorption layer of hexamethyldisilazane. A stearic acid ($CH_3(CH_2)_{16}COOH$) LB film was further formed, as a monomolecular film, on the adsorption layer. The resultant was used as a sample. This sample had carboxyl groups (—COOH) exposed on its surface in water.

The pH value of the solution in the measurement cell was set to be 7, and voltages of +1.2 V to −0.2 V were applied to the cantilever with respect to the silver-silver chloride reference electrode to detect electrostatic forces.

Figure 5:
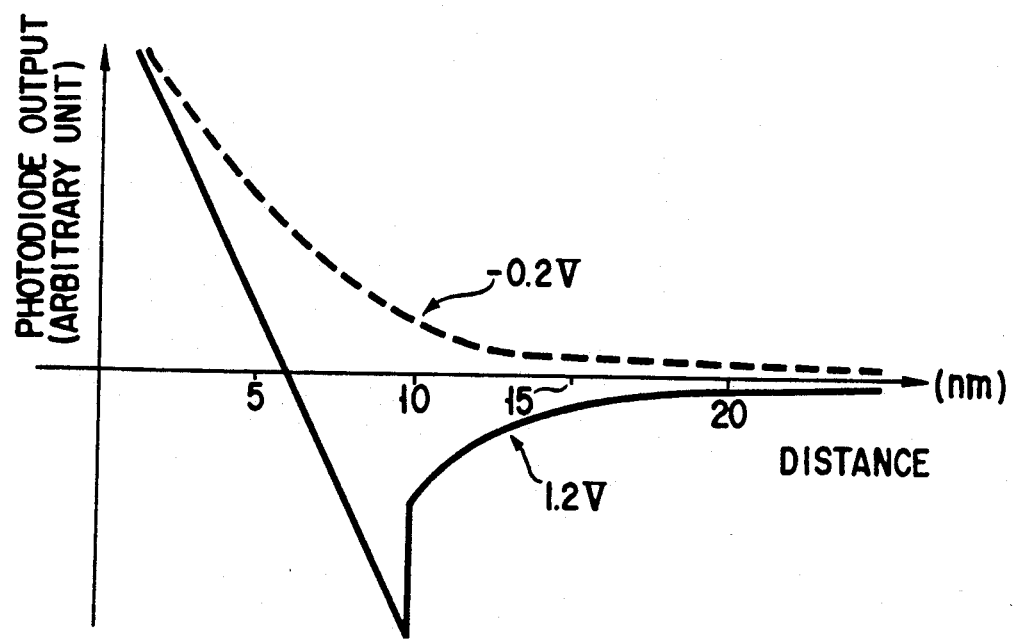
FIG. 5 is a graph showing the relationship between the sample moving distance in the vertical direction and the photodiode output, which are detected with respect to a sample consisting of a stearic acid LB film by using the apparatus in FIG. 3.

FIG. 5 shows the result of force-curve measurement for an electrostatic force when a DC voltage of +1.2 V or −0.2 V was applied to the cantilever. In FIG. 5, the abscissa indicates the moving distance of the sample in the vertical direction and the ordinate indicates the photodiode output corresponding to the displacement of the cantilever. A change in photodiode output at +1.2 V is represented by a solid line, while a change at −0.2 V is represented by a broken line. As is evident from FIG. 5, when the voltage was +1.2 V, an attractive force acted. The jump-in phenomenon was caused at the moment where the sample had just moved 10 nm in the vertical direction resulting in contact of the tip of the cantilever and the sample. On the other hand, when the voltage was −0.2 V, an repulsive force acted. The attractive force acting due to the application of +1.2 V and the repulsive force acting due to the application of −0.2 V correspond to the electrostatic force built up between the negatively charged $COO^-$ and the charge at the tip end of the cantilever.

Figure 6:
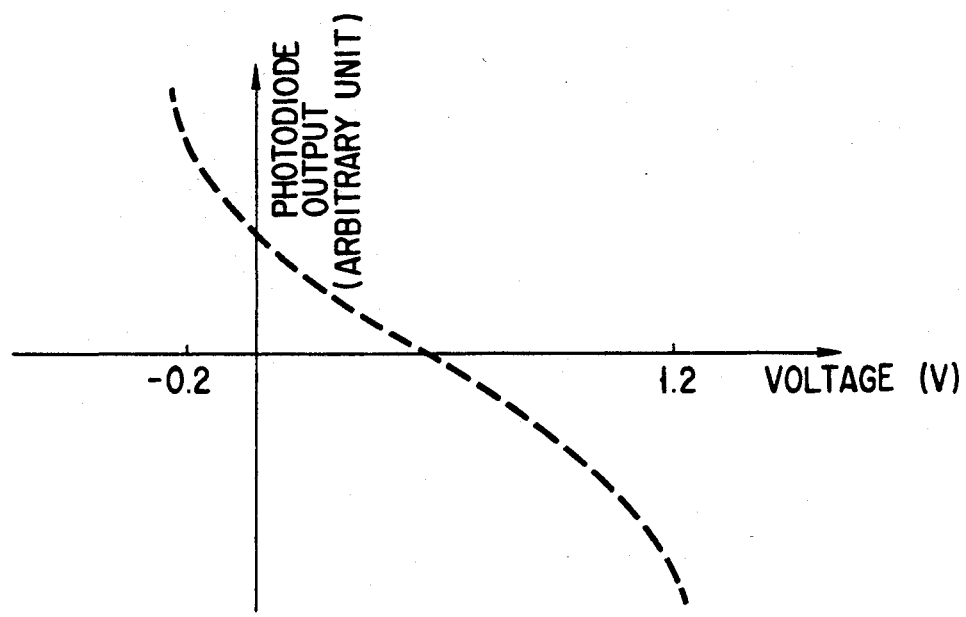
FIG. 6 is a graph showing the relationship between the voltage applied to the cantilever and the photodiode output, which are detected with respect to a sample consisting of a stearic acid LB film by using the apparatus in FIG. 3.

FIG. 6 represents the relationship between the voltage applied to the cantilever and the photodiode output corresponding to the displacement of the cantilever. This data was acquired by applying a triangular voltage having a frequency of 0.25 Hz to the cantilever when the sample had just moved 15 nm in the vertical direction in FIG. 5. In FIG. 6, the voltage-displacement characteristic curve slightly deviates from a straight line. The reason for such a deviation may be that the charge in the functional group of $—COO^-$ is polarized by the voltage. In addition, a point at which the force becomes 0 is located in the positive region of the applied voltage. This is because the chemical potential of Au coated on the cantilever surface is different from that of the solution.

It was confirmed that the cantilever displacement did not change with respect to the change in voltage when the frequency of the applied triangular voltage was set to be 5 MHz. The reason for this may be that since the frequency of the applied AC voltage is high, ions in the solution do not satisfactorily respond, and the structure of electric double layer near the cantilever surface dose not change.

EXPERIMENT 3

Sample was prepared following the same procedures as in Experiment 2 except that a stearylamine ($CH_3(CH_2)_{17}NH_2$) LB film was used as an LB film. This sample had an amino group (—$NH_2$) exposed on its surface in water.

Figure 7:
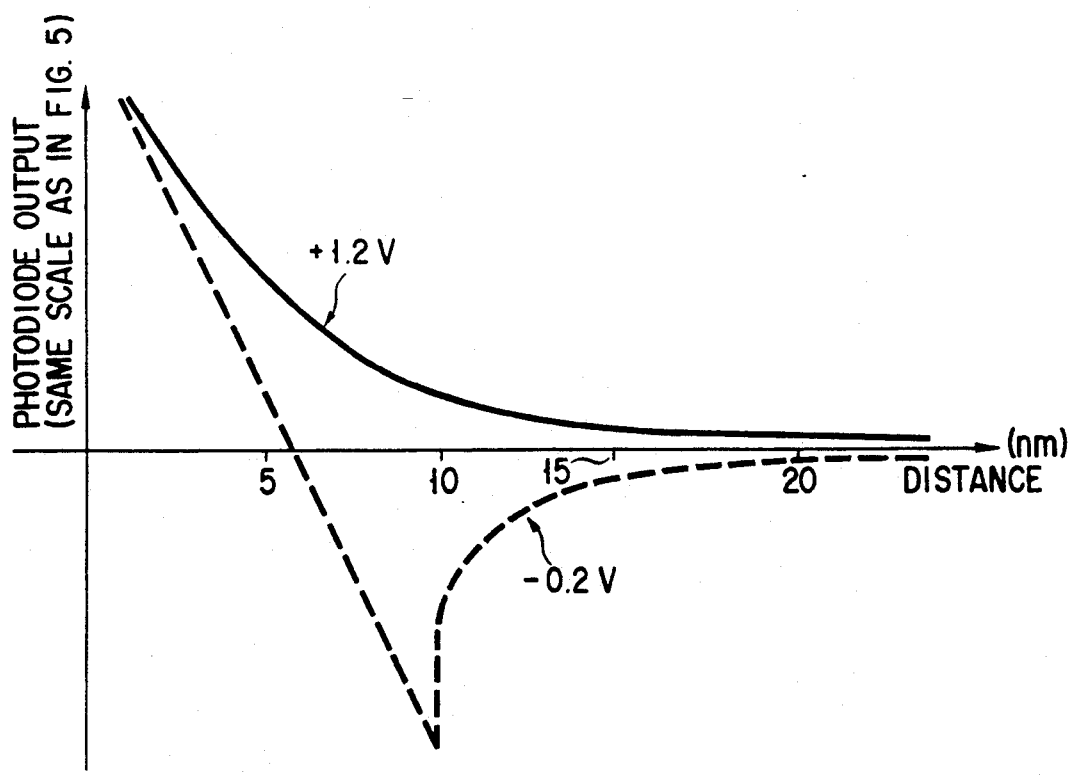
FIG. 7 is a graph showing the relationship between the sample moving distance in the vertical direction and the photodiode output, which are detected with respect to a sample consisting of a stearylamine LB film by using the apparatus in FIG. 3.
Figure 8:
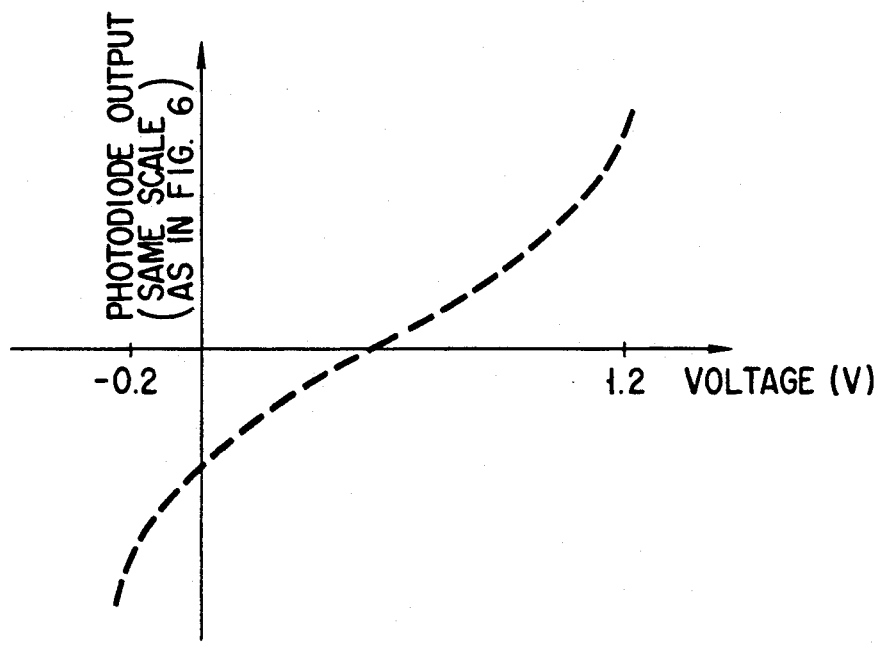
FIG. 8 is a graph showing the relationship between the voltage applied to the cantilever and the photodiode output, which are detected with respect to a sample consisting of a stearylamine LB film by using the apparatus in FIG. 3.

The pH value of the solution in the measurement cell was set to be 7, and a DC voltage of +1.2 V or −0.2 V was applied to the cantilever with respect to the silver/silver chloride reference electrode to detect an electrostatic force. FIG. 7 shows the result. Referring to FIG. 7, unlike the case shown in FIG. 5, it is clear that when a positive voltage is applied to the cantilever, a repulsive force acts, and that when a negative voltage is applied, an attractive force acts. This result indicates that the cantilever is displaced by the electrostatic force acting between the positively charged —$NH_3^+$ and the charge at the tip end of the cantilever. FIG. 8 shows the relationship between the applied voltage and the photodiode output. It is apparent that the relationship between the voltage and the displacement is also opposite to that shown in FIG. 6.

EXPERIMENT 4

A sample was prepared following the same procedures as in Experiment 2 except that a stearylamide $CH_3(CH_2)_{16}CONH_2$ LB film was used as an LB film. This sample had an amide group (—$CONH_2$) exposed on its surface in water.

Figure 9:
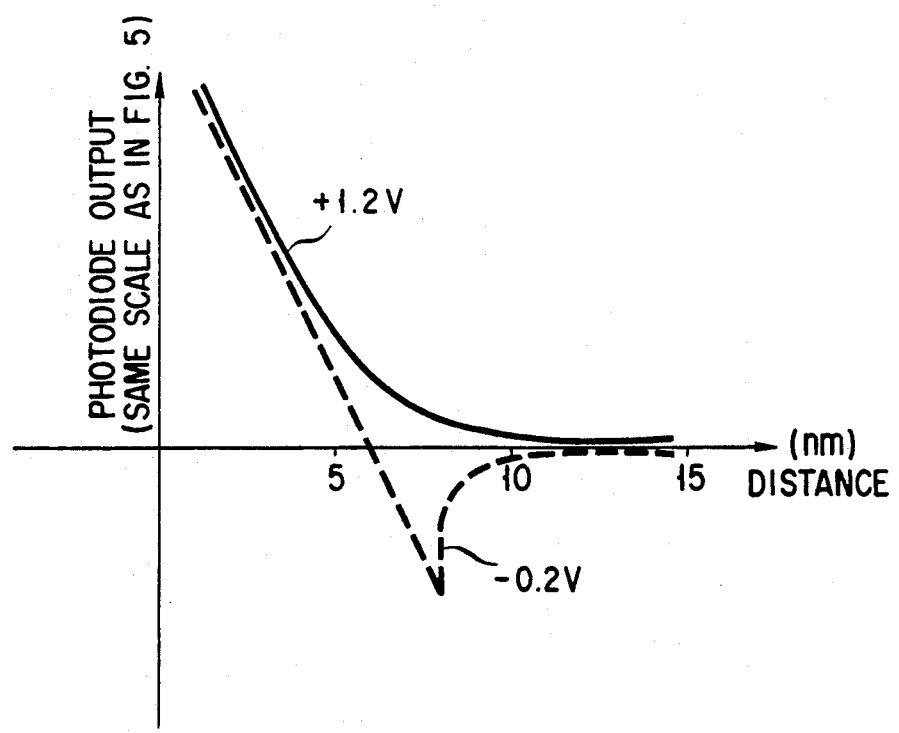
FIG. 9 is a graph showing the relationship between the sample moving distance in the vertical direction and the photodiode output, which are detected with respect to a sample consisting of a stearylamide LB film by using the apparatus in FIG. 3.

The pH value of the solution in the measurement cell was set to be 7, and triangular voltages of +1.2 V to −0.2 V were applied to the cantilever with respect to the silver/silver chloride reference electrode to detect electrostatic forces. FIG. 9 shows the result. Referring to FIG. 9, it is clear that the electrostatic force is reduced as compared with the case of an ionized functional group such as —$COO^-$ or —$NH_3^+$. In addition, when the voltage applied to the cantilever is positive, a repulsive force acts, and when the voltage is negative, an attractive force acts. The relationship between the polarity of a voltage and the force is the same as that in Experiment 3. This result is obtained because the tip end of the cantilever is located closest to an H atom, of the amide group, which has a positive atomic charge.

Figure 10:
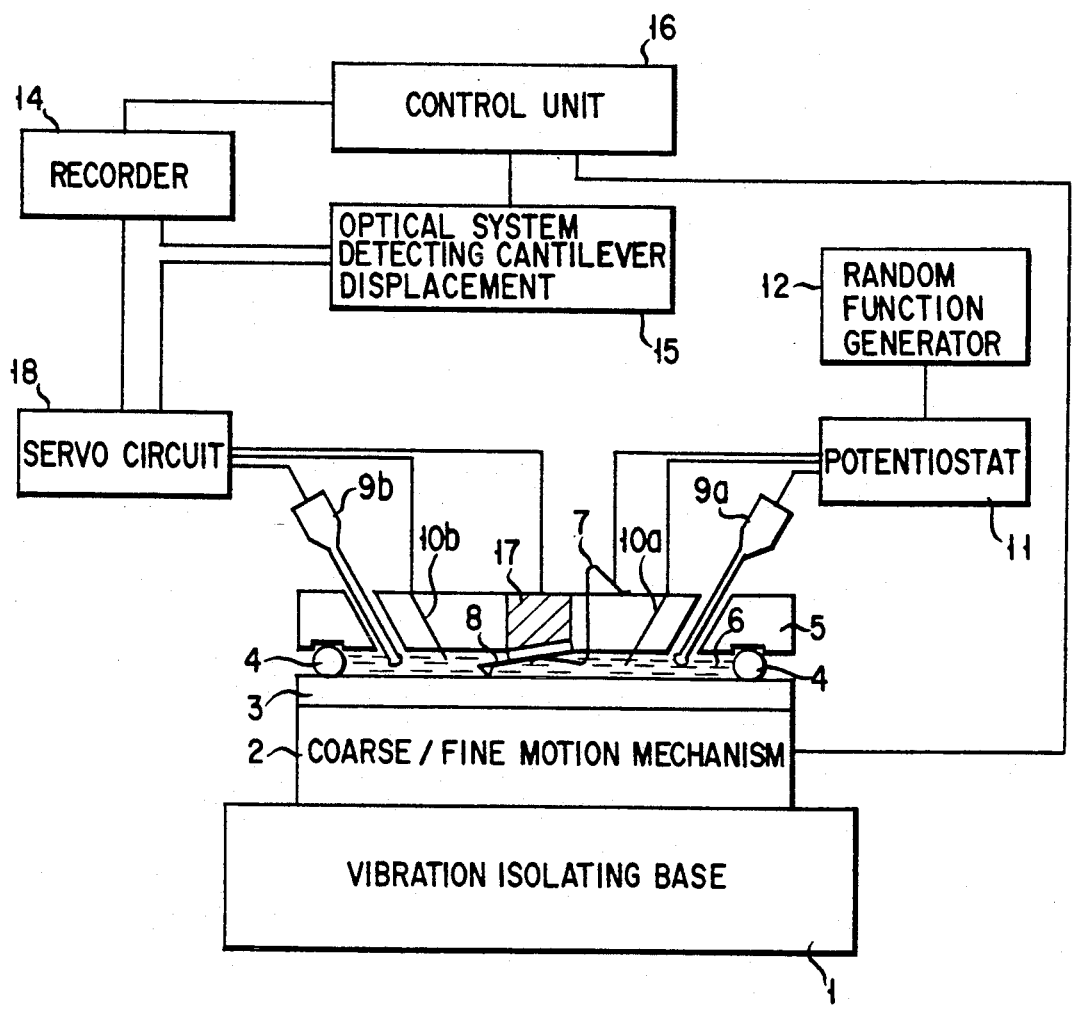
FIG. 10 is a view showing the arrangement of an apparatus for detecting an electrostatic force according to another embodiment of the present invention.

FIG. 10 shows the arrangement of an apparatus for detecting an electrostatic force in a solution according to another embodiment of the present invention. FIGS. 11A and 11B are sectional views of a cantilever 8 constituting the apparatus. The cantilever 8 is constituted by a base member 21 consisting of $Si_3N_4$ and having a tip in the form of a quadrangular cone on its end, and 100-nm thick Au films 22 formed on the two surfaces of the cantilever 8 to be insulated from each other. The arrangement of the apparatus shown in FIG. 10 is almost the same as that of the apparatus shown in FIG. 3 except that voltages are independently applied to the Au films formed on the two surfaces of the cantilever 8. A description of portions common to the apparatuses shown in FIGS. 3 and 10 will be omitted, and only different portions will be described below.

A working electrode 17 constituted by a stainless base member having a surface covered with Au is fixed to a groove portion formed in the lower surface of a holder 5 with which the back-side surface of the supported portion of the cantilever 8 is in contact. Reference and counter electrodes 9a and 10a for applying a voltage to the Au film on the tip-side surface of the cantilever 8, and reference and counter electrodes 9b and 10b for applying a voltage to the Au film on the back-side surface of the cantilever 8 are dipped in an aqueous solution 6 in a measurement cell. As the reference electrodes 9a and 9b, calomel electrodes or silver/silver chloride electrodes are used. As the counter electrodes 10a and 10b, Pt wires are used.

A clip 7, the reference electrode 9a, and the counter electrode 10a are connected to a voltage application system constituted by a potentiostat 11 and a function generator 12. The working electrode 17, the reference electrode 9b, and the counter electrode 10b are connected to a voltage application system constituted by a servo circuit 18. With this arrangement, different voltages can be applied to the Au films 22 and 23 on the two surfaces of the cantilever 8, respectively, while they are controlled.

The displacement of the cantilever 8 is detected, as a photodiode output, by a cantilever displacement detecting optical system 15. A voltage is applied to the back-side surface of the cantilever 8 so as to keep the photodiode output constant. The magnitude of a very small attractive force acting between the tip and the sample surface is obtained from the magnitude of a voltage applied to the back-side surface of the cantilever 8. The voltage applied to the back-side surface of the cantilever 8 and the displacement of the cantilever 8 are synchronously detected by a phase-sensitive detector 13 and are recorded on a recorder 14.

In Experiments 5 and 6, which will be described below, a cantilever constituted by an $Si_3N_4$ base member having 100-nm thick Au films formed on its two surfaces by vapor deposition to be insulated from each other, as shown in FIG. 11, was used.

EXPERIMENT 5

A sample of stearic acid LB film was used as in Experiment 2, and the magnitude of a voltage applied to the back-side surface of the cantilever was controlled to keep the cantilever displacement constant. The pH value of the solution in the measurement cell was set to be 7, and a voltage of +1.2 V was applied to the tip-side surface of the cantilever with respect to the silver/silver chloride reference electrode to detect an electrostatic force. FIG. 12 shows the result. In FIG. 12, the abscissa indicates the vertical moving distance of the sample corresponding to the distance between the tip end and the sample surface, and the ordinate indicates the magnitude of a very small attractive force acting between the tip and the sample surface, which is calculated on the basis of the difference between the voltages applied to the two surfaces of the cantilever. Referring to FIG. 12, unlike the case shown in FIG. 5 which is the result of Experiment 2, it is clear that a force curve attributable to the very small electrostatic attractive force acting between the tip end and the sample surface can be obtained without causing "jump-in" even in the region where the distance between the tip end and the sample surface is 5 nm or less. In addition, since the cantilever displacement is kept constant, the abscissa accurately reflects the distance between the tip end and the sample surface.

On the other hand, a voltage of −0.2 V was applied to the tip-side surface of the cantilever, and the magnitude of the voltage applied to the back-side surface of the cantilever was controlled to keep the cantilever displacement constant. Under these conditions, an electrostatic force was detected. FIG. 13 illustrates the result. As shown in FIG. 13, a repulsive force was detected. In this case, the force-distance relationship obtained was more accurate than that illustrated in FIG. 5. This is because the cantilever displacement is maintained constant, the abscissa accurately reflects the distance between the tip end and the sample surface.

EXPERIMENT 6

A stearylamine LB film was used as sample as in Experiment 3, and the magnitude of the voltage applied to the back-side surface of the cantilever such that the displacement of the cantilever remained constant. The pH value of the solution in the measurement cell was set at 7, and a voltage of −0.2 V was applied to the tip-side surface of the cantilever with respect to the silver/silver chloride reference electrode. Under these conditions, electrostatic forces were detected. The result is shown in FIG. 14. As shown in FIG. 14, no jump-in occurred even when the distance between the tip end and the sample surface was very short, unlike in Experiment 3 the results of which are represented in FIG. 7. As is evident from FIG. 14, the electrostatic force between the negative charge at the tip end and $-NH_3^+$ group on the stearylamine LB film was observed in detail.

EXPERIMENT 7

Use was made of a cantilever which had a tip-side surface covered with polar functional groups and a backside surface covered with Au, as is illustrated in FIGS. 15A and 15B. The tip-side surface had been covered with the functional groups by washing a SiN cantilever with nitric acid, keeping the SiN cantilever in a toluene solution containing 5% of 3-aminopropyltriethoxysilane, $(EtO)_3Si(CH_2)_3NH_2$, for 24 hours, and thoroughly washing the cantilever with water.

In this experiment, the apparatus shown in FIG. 10 was used, but no voltage was applied to the tip-side surface of the cantilever. A stearic acid LB film was used as sample, as in Experiments 2 and 5, and the pH value of the solution in the measurement cell was set at 7. The cantilever and the sample were moved close to each other, whereby an attractive force started acting at a specific position. Thereafter, the cantilever and the sample were further moved close to each other, while the magnitude of the voltage applied to the back-side surface was controlled such that the displacement of the cantilever remained constant. The force between the tip and the sample was measured during such a procedure. The result is shown in FIG. 16. In FIG. 16, the abscissa indicates the vertical moving distance of the sample corresponding to the distance between the tip end and the sample surface. This distance accurately represented the distance between the tip and the sample surface since the displacement of the cantilever was maintained constant. In FIG. 16, the ordinate indicates the magnitude of a very small attractive force acting between the tip and the sample surface, which is calculated on the basis of the voltage applied to the cantilever. As is evident from FIG. 16, an attractive force can be detected without causing any jump-in. This attractive force is the electrostatic force acting between $-HN_3^+$ group on the tip end and $-COO^-$ group on the sample surface.

EXPERIMENT 8

The cantilever shown in FIGS. 15A and 15B was used, measuring the force between the tip and a stearylamine LB film used as sample, while controlling the voltage applied to the back-side surface of the cantilever, as in Experiment 7. The result is shown in FIG. 17. As is clearly seen in FIG. 17, an electrostatic repulsive force was detected, acting between $-NH_3^+$ group on the tip end and $-NH_3^+$ group on the sample surface.

As can be understood from the results of Experiments 7 and 8, an electrostatic force reflecting the charged condition of the functional groups on the sample surface can be detected, thereby identifying the functional group, even if use is made of a cantilever having the structure shown in FIGS. 15A and 15B.

As has been described in detail above, by using the apparatus for detecting electrostatic force in a solution of the present invention, an electrostatic force reflecting the charged or polarized state of a functional group on a sample surface can be detected, and hence the functional group can be identified. In addition, even if the tip end and a sample surface are located at a very short distance, a very small attractive force acting between them can be detected.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An apparatus for detecting an electrostatic force in a solution having a sample and a cantilever placed in the solution and designed to detect a force acting between the sample and a tip on the end of the cantilever, comprising:
   a cantilever having a end portion whose surface is made of a conductive material;
   means for applying a voltage to the conductive material on the cantilever end portion; and
   means for controlling the voltage applied to the conductive material on the cantilever end portion.

2. The apparatus according to claim 1, wherein said cantilever consists of a base member made of an insulating material and conductive films formed on a tip-side surface and a back-side surface of the cantilever end portion to be connected to each other.

3. The apparatus according to claim 2, wherein said conductive films formed on the tip-side surface and the back-side surface of the cantilever end portion have the same area projected onto the surface of the cantilever.

4. The apparatus according to claim 1, wherein said means for applying the voltage to the conductive material on the cantilever end portion is an AC power supply.

5. The apparatus according to claim 1, wherein said means for controlling the voltage applied to the conductive material on the cantilever end portion comprises a potentiostat connected to a three-electrode system constituted by the conductive material on the cantilever end portion, a reference electrode, and a counter electrode.

6. The apparatus according to claim 1, further comprising means for synchronously detecting a voltage applied to said cantilever and a displacement of said cantilever.

7. The apparatus according to claim 1, wherein a functional group exists on a surface of the sample.

8. An apparatus for detecting an electrostatic force in a solution having a sample and a cantilever placed in the solution and designed to detect a force acting between the sample and a tip on the end of the cantilever, comprising:
   a cantilever having conductive films respectively formed on a tip-side surface and a back-side surface of the cantilever end portion to be insulated from each other;
   means for independently applying voltages to the conductive films on the two surfaces of the cantilever end portion; and
   means for independently controlling the voltages applied to the conductive films on the two surfaces of the cantilever end portion.

9. The apparatus according to claim 8, wherein a displacement of said cantilever is kept constant by said means for independently applying the voltages to the conductive films on the two surfaces of the cantilever end portion and said means for independently controlling the voltages applied to the conductive films on the two surfaces of the cantilever end portion.

10. An apparatus for detecting an electrostatic force in a solution having a sample and a cantilever placed in the solution and designed to detect a force acting between the sample and a tip on the end of the cantilever, comprising:
    a cantilever having an end portion where polar functional groups are formed on a tip-side surface and a conductive film is formed on a back-side surface, said polar functional groups serving to generate an electrostatic force between said functional groups and the surface of the sample;
    means for applying a voltage to the conductive film on the back-side surface of the cantilever end portion; and
    means for controlling the voltage applied to the conductive film on the back-side surface of the cantilever end portion.

11. The apparatus according to claim 10, wherein a displacement of said cantilever is kept constant by said means for applying the voltage to the conductive film on the back-side surface of the cantilever end portion and said means for controlling the voltage applied to the conductive film on the back-side surface of the cantilever end portion.

12. An apparatus according to claim 10, wherein said polar functional groups are selected from the group consisting of $-COOM_2$, (M: alkali metal), $-SO_3H$, $-NH_2$, $-COOHN_2$, $-OH$, $-COOH$, $-COOM$ (M: divalent metal), $-CO$, $-COH$, $-NO_2$, $-PO_3H$, and $-CN$.

* * * * *